US 6,732,773 B2

(12) United States Patent
Renz

(10) Patent No.: US 6,732,773 B2
(45) Date of Patent: May 11, 2004

(54) COVER ASSEMBLY FOR USE WITH A BREAST MILK STORAGE SYSTEM

(75) Inventor: Charles John Renz, Briarcliff Manor, NY (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 10/173,966

(22) Filed: Jun. 18, 2002

(65) Prior Publication Data

US 2003/0230351 A1 Dec. 18, 2003

(51) Int. Cl.[7] ................................................ A61M 1/00
(52) U.S. Cl. .............................. 141/384; 141/2; 141/18; 141/383; 604/74
(58) Field of Search ..................... 141/2, 18, 21, 141/25–28, 383, 384, 386; 604/74–76

(56) References Cited

U.S. PATENT DOCUMENTS

| D53,182 S | 4/1919 | Roberts |
| D174,205 S | 3/1955 | Ward ............................ 58/26 |
| 2,911,128 A | 11/1959 | Krautkrämer ............... 222/543 |
| 2,958,439 A | 11/1960 | Yochem .................... 220/38.5 |
| 3,145,872 A | 8/1964 | Hayes ........................ 220/60 |
| 3,256,892 A | 6/1966 | Esposito, Jr. ................ 132/83 |
| 3,407,956 A | 10/1968 | Linkletter .................... 215/41 |
| 3,419,179 A | 12/1968 | Deuschle et al. .......... 220/38.5 |
| 3,911,920 A * | 10/1975 | Susinn ......................... 604/75 |
| 4,548,332 A | 10/1985 | Neat ........................... 220/268 |
| 4,638,916 A | 1/1987 | Beck et al. .................. 215/235 |
| 4,713,219 A | 12/1987 | Gerken et al. .............. 422/102 |
| 4,753,358 A | 6/1988 | Virca et al. ................. 215/230 |
| 5,071,403 A * | 12/1991 | Larsson ....................... 604/74 |
| 5,178,308 A | 1/1993 | Endre ......................... 224/32 |
| 5,361,918 A | 11/1994 | Mason .......................... 215/6 |
| D353,328 S | 12/1994 | Nuffer ........................... 9/446 |
| 5,407,093 A | 4/1995 | McGill ....................... 220/666 |
| 5,462,101 A * | 10/1995 | Mouchmouchian ......... 141/364 |
| 5,472,025 A * | 12/1995 | Conrad et al. .............. 141/332 |
| 5,604,101 A | 2/1997 | Hanley et al. ................. 435/6 |
| 5,653,353 A | 8/1997 | Otto et al. ................... 215/306 |
| 5,667,094 A | 9/1997 | Rapchak et al. ............ 220/339 |
| 5,720,722 A * | 2/1998 | Lockridge .................... 604/74 |
| 5,753,186 A | 5/1998 | Hanley et al. ............... 422/101 |
| 5,843,029 A * | 12/1998 | Bachman et al. ............. 604/74 |
| 5,848,623 A * | 12/1998 | Ueda ........................... 141/64 |
| 5,878,898 A | 3/1999 | Shefflin ..................... 215/11.6 |
| D411,106 S | 6/1999 | Conrad .......................... 9/436 |
| 5,950,689 A * | 9/1999 | Varlet .......................... 141/22 |
| 6,116,439 A | 9/2000 | Yaniv ........................ 215/11.1 |
| D435,444 S | 12/2000 | Newville et al. ............... 9/446 |
| 6,206,223 B1 | 3/2001 | Wicker ....................... 220/375 |
| 6,461,324 B1 * | 10/2002 | Schlensog .................... 604/74 |
| 2001/0013499 A1 | 8/2001 | Morano et al. ............ 215/11.6 |

FOREIGN PATENT DOCUMENTS

| BE | 507674 | 7/1951 | |
| DE | 695403 | 3/1951 | |
| FR | 937248 | 4/1946 | ..................... 20/4 |

* cited by examiner

Primary Examiner—J Casimer Jacyna
(74) Attorney, Agent, or Firm—Ohlandt, Greeley, Ruggiero & Perle, LLP

(57) ABSTRACT

A cover assembly for use with a breast milk storage system is produced having a hollow double threaded main body and a removable sealing cap. The cover assembly cooperates with a fluid pump mechanism to enable the efficient and effective transfer of breast milk from a mother's breast to a fluid storage container. The cover assembly eliminates the need for additional cleanup and reduces the risk of spilling the breast milk, as well as the risk of contamination, during the process of storing breast milk.

24 Claims, 4 Drawing Sheets

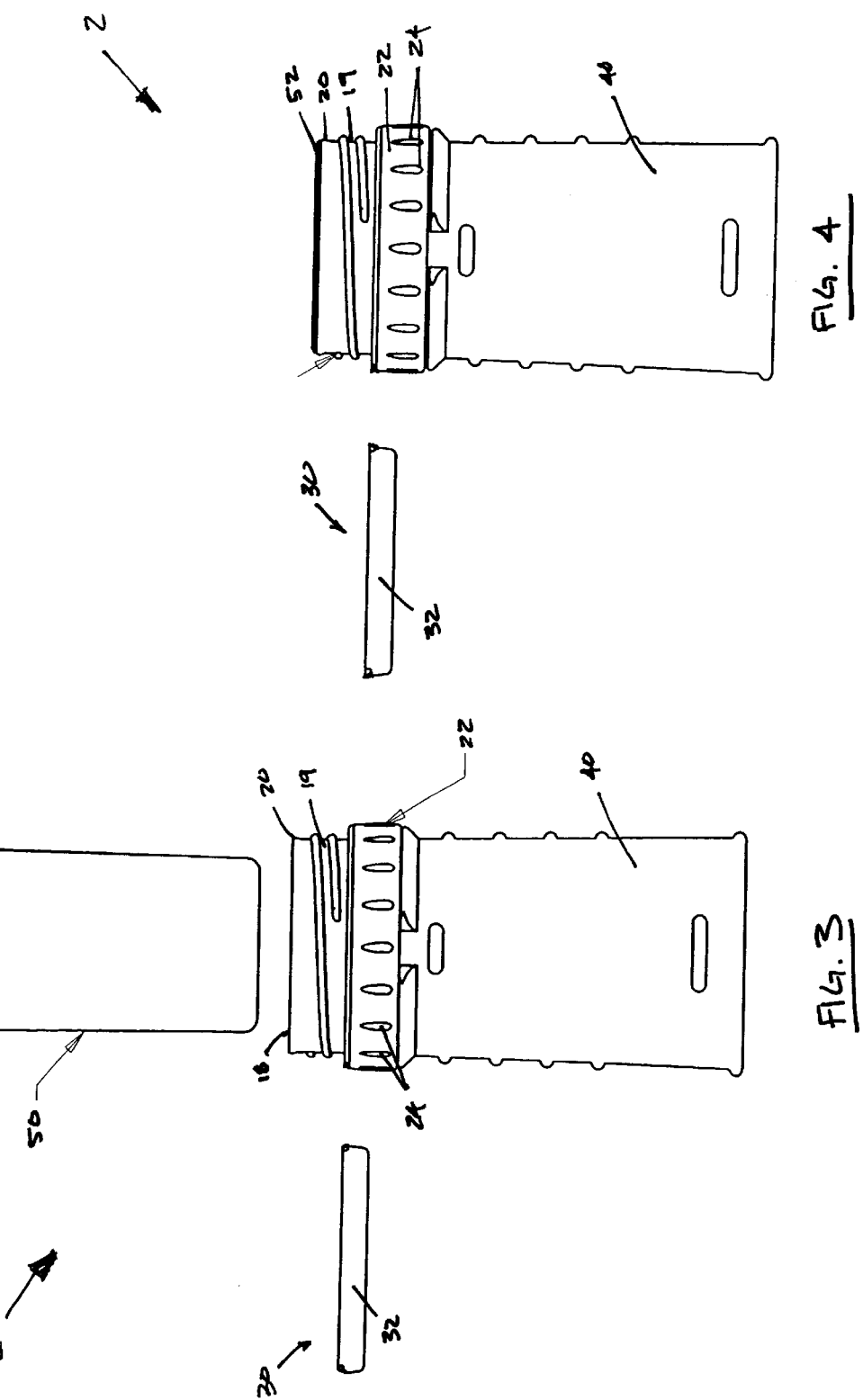

COVER ASSEMBLY FOR USE WITH A BREAST MILK STORAGE SYSTEM

BACKGROUND OF THE INVENTION

1. Field of the Invention

The present invention relates to a cover assembly. More particularly, the present invention relates to a cover assembly for use with a breast milk storage system.

2. Description of the Prior Art

Breast milk storage systems are known in the art. The conventional devices and methods require, at a minimum, a rigid reusable container, a separate flexible storage container, and a clip or twist tie for sealing the flexible storage container. The process employing these devices to store breast milk is inefficient, requiring extra steps. For example, the process of transferring the breast milk from the rigid reusable container to the storage container can necessitate additional clean up and lead to the breast milk being wasted if it is spilled or contaminated during the process. Also, the process requires a user to place and remove the clip or twist tie from the storage container in order to gain access to the breast milk and transfer the milk to a feeding bottle.

Given the difficulty inherently associated in the process of obtaining breast milk using a breast pump, the loss of breast milk due to spillage or contamination, is a concern. Also, given the health implications for an infant, the cleanliness and sterilization of the components of the system are of significant concern.

Thus, there is a need to provide a cover assembly for use with a breast milk storage system that eliminates the need for additional cleanup and reduces the risk of spilling the breast milk, as well as the risk of contamination, during the breast milk storing process.

SUMMARY OF THE INVENTION

It is an object of the present invention to provide a cover assembly for facilitating the easy and efficient transfer of breast milk from a pumping mechanism to a storage container.

It is another object of the present invention to provide such a cover assembly that provides for integral connection of a breast pump to a storage container.

It is still another object of the present invention to provide such a cover assembly that provides for selective sealing of a storage container.

It is yet another object of the present invention to provide a cover assembly that reduces the risk of spillage and contamination during the process of collecting and storing breast milk.

These and other objects and advantages of the present invention are achieved by a cover assembly of the present invention. The cover assembly has a hollow main body and a sealing cap. The hollow main body preferably has an annular lower portion with a threaded inner surface that cooperates with a threaded open end of a fluid storage container, and an upper portion with a threaded outer surface that cooperates with a threaded open end of a pump mechanism. The upper portion also has a shoulder with an outwardly projecting lip or flange. The sealing cap preferably has a sidewall with an inner flange running about an inner surface thereof. The inner flange of said sealing cap cooperates with the outer flange of the upper opening of the main body to selectively seal the upper opening of the main body and the fluid storage container. Thus, the present invention provides for a cover assembly that first, facilitates the easy and efficient transfer of a fluid from a fluid pump mechanism to a fluid storage container and second, enables the fluid storage container to be easily and efficiently sealed, detached and stored.

BRIEF DESCRIPTION OF THE DRAWINGS

FIG. 3 is an exploded, first side view of a holder and a removable storage container that cooperate with the cover assembly of FIG. 1;

FIG. 4 is an exploded, second side view of the holder of FIG. 3, showing the removable storage container inserted into the holder and supported by the main body of the cover assembly of FIG. 1;

DETAILED DESCRIPTION OF THE INVENTION

Figure 1:
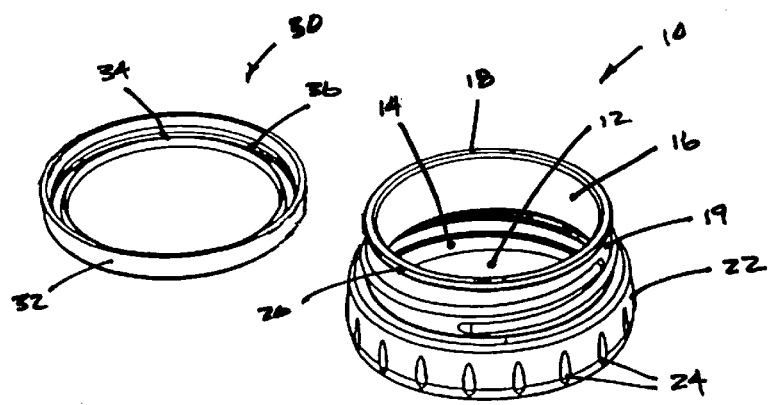
FIG. 1 is a perspective, exploded view of a cover assembly having a main body and a sealing cap, in accordance with a preferred embodiment of the present invention.
Figure 2:
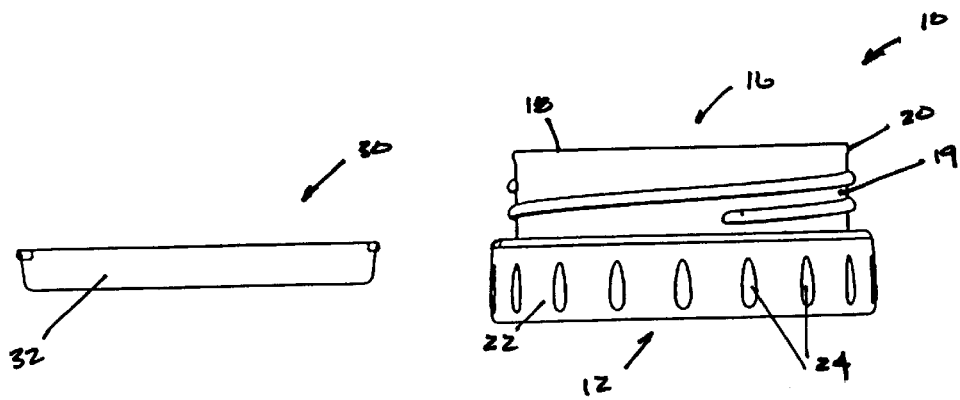
FIG. 2 is a side, exploded view of the cover assembly of FIG. 1.
Figure 6:
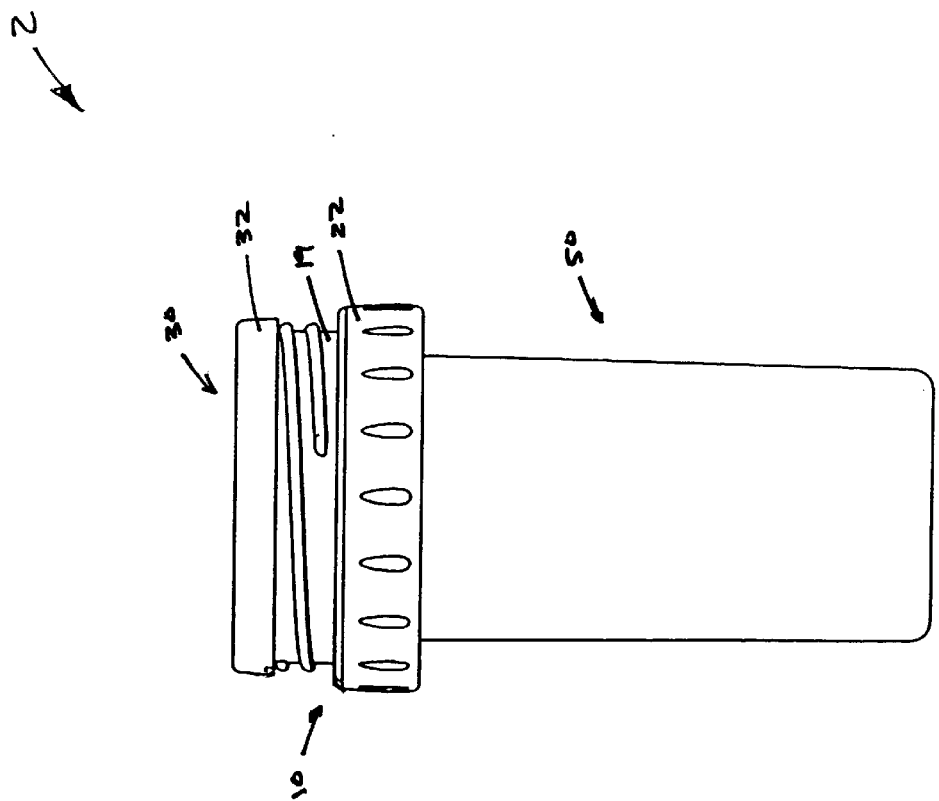
FIG. 6 is a side view showing the cover assembly connected with the removable storage container and removed from the holder for storage.
Figure 5:
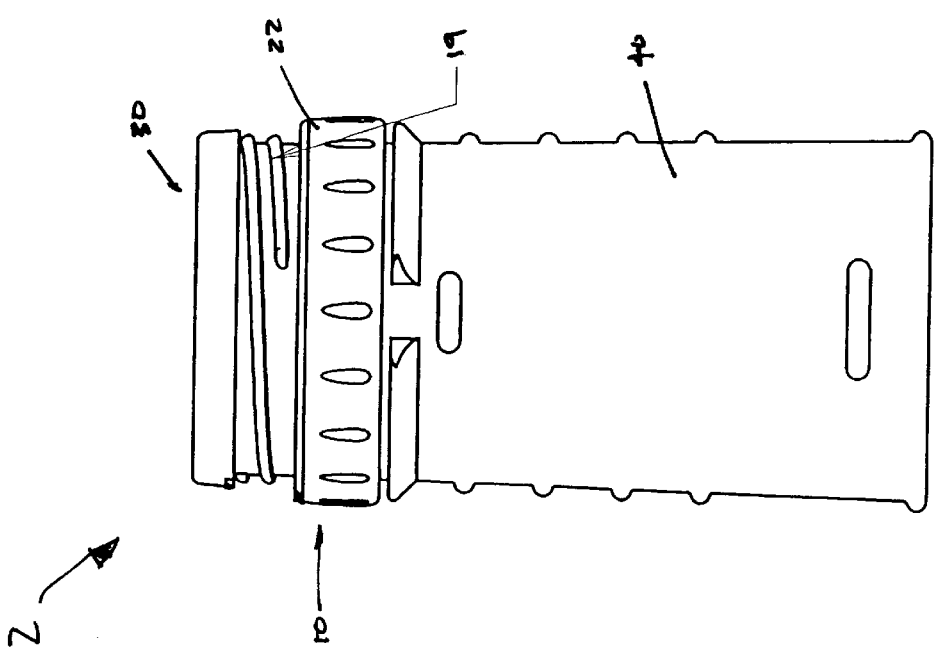
FIG. 5 is a third side view of the holder of FIG. 3, showing the sealing cover of the cover assembly connected to an upper opening of the main body of the cover assembly securing the removable storage container with the cover assembly and sealing the removable storage container closed.

Referring to the drawings and, in particular FIGS. 1 and 2, there is shown a cover assembly for use with a breast milk storage system in accordance with a preferred embodiment of the present invention generally represented by reference numeral 1. Cover assembly 1 preferably has a hollow double threaded main body 10 and a removable sealing cap 30.

Preferably, main body 10 has a lower opening 12 with an outer surface 22 having a number of gripping structures 24 integrally formed thereon and a threaded inner surface 14. Preferably, lower opening 12 is configured to connect to and cooperate with a fluid storage container 2 (clearly shown in FIG. 3). Preferably, gripping structures 24 are spaced sufficiently to enable a user to readily grip main body 10 with their fingers to facilitate connecting and disconnecting main body 10 with storage container 2. Preferably, lower opening 12 can be of any shape or size necessary to effectively connect with different fluid storage containers.

Preferably, main body 10 has an upper opening 16 that forms a shoulder 18 and has a threaded outer surface 19. Preferably, upper opening 16 is configured to connect to and cooperate with a fluid or breast milk pump mechanism (not shown). Shoulder 18 of upper opening 16 preferably has an outwardly projecting lip or flange 20. Preferably, upper opening 16 can also be of any shape or size necessary to effectively connect with different breast pump mechanisms.

Preferably, main body 10 is formed from a sturdy material such as a rigid polypropylene. Also preferably, main body 10 cooperates with the breast pump mechanism and the fluid storage container to integrally connect the same and facilitate the effective and efficient transfer of breast milk from a mother's breast to the fluid storage container.

Still referring to FIGS. 1 and 2, sealing cap 30 preferably has a sidewall 32 with an inner flange 34 running about an inner surface 36 thereof. Inner flange 34 preferably is integrally formed with sealing cap 30 and cooperates with outer flange 20 of upper opening 16 of main body 10 to selectively engage and seal the upper opening with the sealing cap 30. Preferably, sealing cap 30 can have different configurations and be formed of any suitable material sufficient to securely connect the sealing cap with main body 10 and to engage and seal fluid storage container 2.

Figure 7:
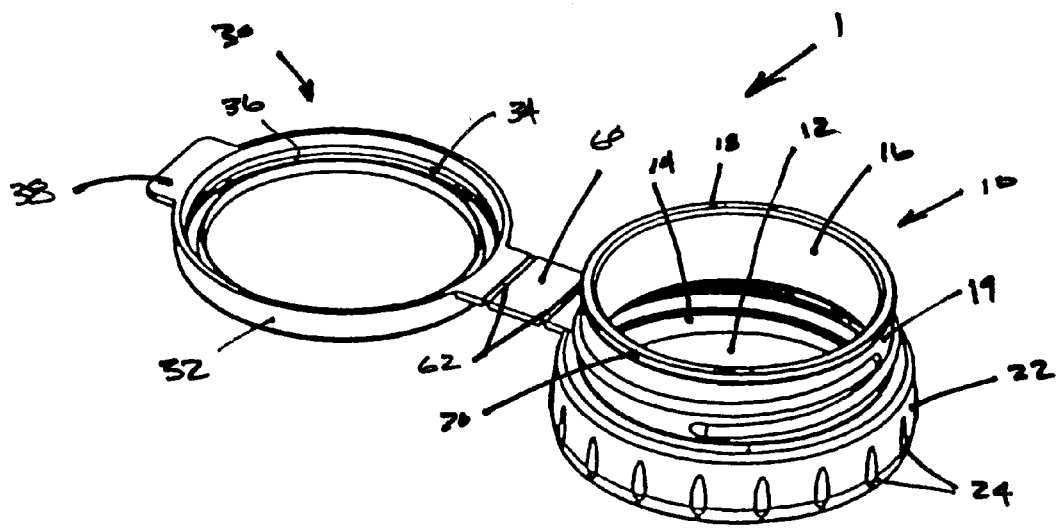
FIG. 7 is a perspective view of the cover assembly, in accordance with an alternative embodiment of the present invention.

As an alternative, sealing cap 30 can have a tab 38 (shown in FIG. 7) that projects outwardly from sidewall 32 to facilitate a user's ability to connect and disconnect the sealing cap with main body 10. Also alternatively, sealing cap 30 may be integrally and flexibly connected to main body 10 by a hinge strap 60 (shown in FIG. 7). Preferably, hinge strap 60 can have at least two grooves 62 optimally spaced to permit at least two pivot points, one at each groove. Preferably, grooves 62 facilitate a more effective seal amongst the sealing cap 30, main body 10 and fluid storage container 2.

Referring to FIG. 3, fluid storage container 2 preferably includes a holder 40 with an upper opening having a threaded outer surface (not shown) and a disposable removable storage container 50 with an upper rim or flange 52. It is noted that fluid storage container 2 can be any suitable structure sufficient to receive and retain a liquid substance and to securely connect with cover assembly 1.

Referring to FIGS. 3 through 6, cover assembly 1 preferably cooperates with holder 40 and removable container 50 to facilitate an efficient process for storing breast milk. Preferably, the first step in the breast milk storage process is to securely engage threaded inner surface 14 of lower opening 12 with threaded upper opening 16 of holder 40. Gripping structures 24 preferably facilitate gripping outer surface 22 to secure the two threaded surfaces. Second, removable container 50 is preferably inserted through cover assembly 1 such that upper flange 52 of the removable container is supported by shoulder 18 of upper opening 16. Third, threaded outer surface 19 of upper opening 16 is preferably interconnected with the threaded opening of the breast pump mechanism. Fourth, breast milk is preferably transferred from the breast pump mechanism to removable container 50. Fifth, the breast pump mechanism is preferably disconnected from upper opening 16. Sixth, upper flange 52 of removable container 50 is preferably secured against shoulder 18 by sealing cap 30 to tightly seal the container closed. Finally, main body 10 and holder 40 are preferably disconnected and cover assembly 1 is removed with container 50 sealed and connected thereto for storage for later use. The cover assembly 1, as illustrated by the above-identified process, effectively eliminates the need for extra containers and alleviates the risk of spillage and/or contamination of breast milk.

The present invention having been thus described with particular reference to the preferred forms thereof, it will be obvious that various changes and modifications may be made therein without departing from the spirit and scope of the present invention as defined in the appended claims.

What is claimed is:

1. A cover assembly comprising:
a main body having a lower opening with a threaded inner surface and an upper opening with a threaded outer surface; and
a sealing cap engageable with said main body to seal said upper opening of said main body so long as said sealing cap is appropriately engaged with said main body;
wherein said main body integrally connects a pump mechanism to a fluid storage container.

2. The cover assembly of claim 1, wherein said pump mechanism is a breast pump and said fluid storage container is suitable for storing breast milk.

3. The cover assembly of claim 1, wherein said threaded inner surface of said lower opening selectively cooperates with a threaded outer surface of an open end of said fluid storage container so as to integrally connect said cover assembly to said fluid storage container.

4. The cover assembly of claim 3, wherein said fluid storage container is a reusable rigid bottle.

5. The cover assembly of claim 3, wherein said fluid storage container is a hollow support structure with a removable disposable container disposed therein.

6. The cover assembly of claim 5, wherein said upper opening of said main body forms a shoulder and said removable disposable container has an upper flange capable of being supported by said shoulder.

7. The cover assembly of claim 6, wherein said upper opening of said main body has an outer flange running about said upper opening such that said outer flange is disposed between said shoulder and said threaded portion of said outer surface.

8. The cover assembly of claim 7, wherein said sealing cap has a sidewall with an inner flange running about an inner surface thereof.

9. The cover assembly of claim 8, wherein said inner flange of said sealing cap cooperates with said outer flange of said upper opening of said main body to selectively seal said upper opening with said sealing cap.

10. The cover assembly of claim 6, wherein said threaded outer surface of said upper opening of said main body selectively cooperates with a threaded inner surface of an outlet of said pump mechanism so as to integrally connect said cover assembly with said pump mechanism.

11. The cover assembly of claim 1, wherein said sealing cap is flexibly connected to said main body by a hinge strap.

12. A fluid storage system comprising:
a fluid storage container with a removable container positioned therein to receive and retain a fluid; and
a cover assembly having a hollow main body with a lower opening having a threaded inner surface, an upper opening having a threaded outer surface, and a sealing cap engageable with said main body to seal said upper opening of said main body so long as said sealing cap is appropriately engaged with said main body;
wherein said lower opening of said main body connects to said fluid storage container and thereby engages said removable container to enable said removable container to be sealed and removed for storage.

13. The fluid storage system of claim 11, wherein said fluid is breast milk.

14. The fluid storage system of claim 11, wherein said threaded outer surface of said upper opening of said main body selectively cooperates with a threaded inner surface of an outlet of a fluid pump mechanism so as to integrally connect said cover assembly with said pump mechanism and allow fluid to be transferred from said pump mechanism to said removable container.

15. The fluid storage system of claim 14, wherein said fluid pump mechanism is a breast pump.

16. The fluid storage system of claim 11, wherein said sealing cap is flexibly connected to said main body by a hinge strap.

17. The fluid storage system of claim 11, wherein said threaded inner surface of said lower opening selectively cooperates with a threaded outer surface of an open end of said fluid storage container so as to integrally connect said cover assembly to said fluid storage container.

18. The fluid storage system of claim 17, wherein said fluid storage container is a rigid baby bottle.

19. The fluid storage system of claim 17, wherein said fluid storage container is a hollow support structure with an upper opening forming a shoulder and wherein said removable container has an upper flange for being supported by said shoulder.

20. The fluid storage system of claim 19, wherein said upper opening of said hollow support structure has an outer flange running about said upper opening such that it is disposed between said shoulder and said threaded portion of said outer surface.

21. The fluid storage system of claim 20, wherein said sealing cap has a sidewall with an inner flange running about an inner surface thereof.

22. The fluid storage system of claim 21, wherein said inner flange of said sealing cap cooperates with said outer flange of said upper opening said main body to selectively seal said upper opening of said main body and said removable container.

23. A method for storing a fluid comprising the steps of:
a) providing a storage container having a holder and a removable container, wherein said holder has an upper opening with a threaded outer surface and said removable container has an upper opening with a flange;
b) providing a cover assembly having a hollow main body and a sealing cap, wherein said main body has a lower opening with a threaded inner surface and an upper opening forming a shoulder and having a threaded outer surface;
c) engaging said threaded outer surface of said holder with said threaded inner surface of said lower opening of said main body to integrally connect said holder to said main body;
d) inserting said removable container through said hollow main body of said cover assembly and into said holder such that said upper flange of said removable container is supported on said shoulder of said upper opening of said main body;
e) engaging said threaded outer surface of said upper opening of said main body with an open end of a fluid pump mechanism having a threaded inner surface to integrally connect said main body to said fluid pump mechanism;
f) transferring fluid from said fluid pump mechanism into said removable container;
g) disengaging said outer and inner threaded surfaces of said main body and said fluid pump mechanism, respectively, and separating said fluid pump mechanism from said cover assembly;
h) sealing said container and said upper opening of said main body with said sealing cap such that said upper flange of said removable container is secured against said shoulder of said upper opening of said main body; and
i) disengaging said threaded inner and outer surfaces of said main body and said holder, respectively, and removing said cover assembly and said removable container from said holder for storage.

24. The method for storing a fluid of claim 23, wherein said fluid pump mechanism is a breast pump and said fluid is breast milk.

* * * * *